US012037370B2

(12) United States Patent
Kudryashov et al.

(10) Patent No.: US 12,037,370 B2
(45) Date of Patent: Jul. 16, 2024

(54) SPLIT-IMMUNOTOXINS FOR BOOSTING ONCOLYTIC VIRUS TOXICITY

(71) Applicants: Ohio State Innovation Foundation, Colimbus, OH (US); Research Institute at Nationwide Children's Hospital, Columbus, OH (US)

(72) Inventors: Dmitri Kudryashov, Columbus, OH (US); Elena Kudryashova, Columbus, OH (US); Vedud Purde, Columbus, OH (US); Timothy Cripe, Dublin, OH (US)

(73) Assignees: Research Institute at Nationwide Children's Hospital, Columbus, OH (US); Ohio State Innovation Foundation, Columbus, OH (US)

( * ) Notice: Subject to any disclaimer, the term of this patent is extended or adjusted under 35 U.S.C. 154(b) by 905 days.

(21) Appl. No.: 16/975,602

(22) PCT Filed: Feb. 26, 2019

(86) PCT No.: PCT/US2019/019621
§ 371 (c)(1),
(2) Date: Aug. 25, 2020

(87) PCT Pub. No.: WO2019/165444
PCT Pub. Date: Aug. 29, 2019

(65) Prior Publication Data

US 2020/0407405 A1 Dec. 31, 2020

Related U.S. Application Data

(60) Provisional application No. 62/635,073, filed on Feb. 26, 2018.

(51) Int. Cl.

| | |
|---|---|
| ***C07K 14/195*** | (2006.01) |
| ***A61K 35/763*** | (2015.01) |
| ***A61P 35/00*** | (2006.01) |
| ***C07K 14/32*** | (2006.01) |
| ***C07K 14/34*** | (2006.01) |
| ***C12N 7/00*** | (2006.01) |

(52) U.S. Cl.
CPC ............ *C07K 14/34* (2013.01); *A61K 35/763* (2013.01); *A61P 35/00* (2018.01); *C07K 14/32* (2013.01); *C12N 7/00* (2013.01); *C07K 2319/55* (2013.01); *C07K 2319/92* (2013.01); *C12N 2710/16642* (2013.01)

(58) Field of Classification Search
None
See application file for complete search history.

(56) References Cited

U.S. PATENT DOCUMENTS

| | | | |
|---|---|---|---|
| 2003/0166004 A1 | 9/2003 | Gyuris et al. | |
| 2004/0091966 A1 | 5/2004 | Zeidler et al. | |
| 2010/0203024 A1 | 8/2010 | Terman et al. | |
| 2016/0136298 A1 | 5/2016 | Grawunder et al. | |

FOREIGN PATENT DOCUMENTS

WO 2015195721 A1 12/2015

OTHER PUBLICATIONS

Alford et al. Conditional Toxin Splicing Using a Split Intein System. Methods Mol Biol. 2017;1495:197-216.*
Kinsella et al. Retrovirally Delivered Random Cyclic Peptide Libraries Yield Inhibitors of Interleukin-4 Signaling in Human B Cells. The Journal of Biological Chemistry, 2002, 277: 37512-37518.*
Lundstrom, K. New frontiers in oncolytic viruses: optimizing and selecting for virus strains with improved efficacy. Biologics. 2018; 12: 43-60. Published online Feb. 9, 2018.*
Agarwal et al. Receptor-Mediated Enhanced Cellular Delivery of Nanoparticles Using Recombinant Receptor-Binding Domain of Diphtheria Toxin. Mol. Pharmaceutics 2017, 14, 1, 23-30.*
Hashimi et al. Immunotoxin-mediated targeting of claudin-4 inhibits the proliferation of cancer cellsInt J Oncol., 2013, 42(6):1911-8.*
International Search Report issued for PCT/US2019/019621 mailed Apr. 26, 2019.
Alford et al., Conditional Toxin Splicing Using a Split Intein System, Methods in Molecular Biology, vol. 1495, p. 197-216, 2016.
Giriat, Izabela, et al., "Protein Semi-Synthesis in Living Cells," J. Am. Chem. Soc., vol. 125 (2003), pp. 7180-7181.
Fitzgerald, David J., et al., "Treatment of Hematologic Malignancies with Immunotoxins and Antibody-Drug Conjugates," Cancer Research, vol. 71 (2011), pp. 6300-6309.
Haque, Samer-ul, et al., "Biologics against cancer-specific receptors—challenges to personalised medicine from early trial results," Current Opinion in Pharmacology, vol. 12 (2012), pp. 392-397.
Kudryashov et al., "Split And Splice" Approach For Highly Selective Targeting Of Human NSCLC Tumors, U.S. Army Medical Research and Materiel Command Fort Detrick, Maryland, pp. 21702-5012.
Cuddington et al., "Permissiveness of human cancer cells to oncolytic bovine herpesvirus 1 is mediated in part by KRAS activity," Journal of Virology, vol. 88 (2014) pp. 6885-6895.

(Continued)

*Primary Examiner* — Nianxiang Zou
(74) *Attorney, Agent, or Firm* — Thomas | Horstemeyer, LLP

(57) ABSTRACT

As disclosed herein, the assistance of a new generation of immunotoxins (split-immunotoxins) the range of cancers susceptible to elimination by oncolytic viruses and the specific toxicity of the latter can be expanded without compromising the selectivity of targeting. To accomplish this goal, a polypeptide chain of a potent bacterial toxin (including, but not limited to a catalytic subunit of a Diphtheria toxin, DTA) can be split into two benign parts, which can then be delivered to the cytoplasm of cancer cells via two independent cancer-specific pathways: (1) together with an oncolytic virus (encoded in its genome); (2) as a split-immunotoxin delivered via receptor-specific toxin entry pathways. The two parts are fused into a functional toxin only in the cytoplasm of dually targeted cancer cells by means of intein-catalyzed trans-splicing.

15 Claims, 12 Drawing Sheets

(56) References Cited

OTHER PUBLICATIONS

Ascierto, Maria Libera, et al., "Permissivity of the NCI-60 cancer cell lines to oncolytic Vaccinia Virus GLV-1h68," BMC Cancer, vol. 11 (2011), p. 451.
Noll et al., Primary resistance phenomena to oncolytic measles vaccine viruses. International journal of oncology 43, 103-112, doi:10.3892/ijo.2013.1914 (2013).
Browne et al., Cancer screening by systemic administration of a gene delivery vector encoding tumor-selective secretable biomarker expression. PloS one 6, e19530, doi:10.1371/journal.pone.0019530 (2011).
Mahller et al., Tissue inhibitor of metalloproteinase-3 via oncolytic herpesvirus inhibits tumor growth and vascular progenitors. Cancer research 68, 1170-1179, doi: 10.1158/0008-5472.CAN-07-2734 (2008).
Maldonado et al., "Molecular engineering and validation of an oncolytic herpes simplex virus type 1 transcriptionally targeted to midkine-positive tumors," The Journal of Gene Medicine, vol. 12 (2010), pp. 613-623.
Potala et al., "Targeted therapy of cancer using diphtheria toxin-derived immunotoxins," Drug Discovery Today, vol. 13, Nos. 17/18 (2008), pp. 807-815.
Yamaizumi, Masaru, et al., "One molecule of diphtheria toxin fragment A introduced into a cell can kill the cell," Cell, vol. 15 (1978), pp. 245-250.
Bell et al., "Crystal structure of diphtheria toxin bound to nicotinamide adenine dinucleotide," Biochemistry, vol. 35 (1996), pp. 1137-1149.
Weidle et al., "Prospects of bacterial and plant protein-based immunotoxins for treatment of cancer," Cancer Genomics Proteomics, vol. 11 (2014), pp. 25-38.
Cheriyan et al., "Faster protein splicing with the Nostoc punctiforme DnaE intein using non-native extein residues," The Journal of Biological Chemistry, vol. 288 (2013), pp. 6202-6211.
Zettler et al., "The naturally split Npu DnaE intein exhibits an extraordinarily high rate in the protein trans-splicing reaction," FEBS Letters, vol. 583 (2009), pp. 909-914.
Chen et al., "Selection of anthrax toxin protective antigen variants that discriminate between the cellular receptors TEM8 and CMG2 and achieve targeting of tumor cells," The Journal of Biological Chemistry, vol. 282 (2007), pp. 9834-9845.
McCluskey et al., "Targeting HER2-positive cancer cells with receptor-redirected anthrax protective antigen," Molecular Oncology, vol. 7 (2013), pp. 440-451.
Mechaly et al., "Changing the receptor specificity of anthrax toxin," mBio , vol. 3 (2012) (6 pages).
Gutwein et al., "Tumor endothelial marker 8 expression in triple-negative breast cancer," Anticancer Res, vol. 31 (2011), pp. 3417-3422.
Smith et al., "Molecular characterization of breast cancer cell lines through multiple omic approaches," Breast Cancer Res, vol. 19 (2017), p. 65.
Krishnamurti, Uma, et al., "HER2 in Breast Cancer: A Review and Update," Adv. Anat. Pathol., vol. 21, No. 2 (2014), pp. 100-107.
Nakai et al., "A perspective on anti-EGFR therapies targeting triple-negative breast cancer," American Journal of Cancer Research, vol. 6 (2016), pp. 1609-1623.
Arora et al., "Fusions of anthrax toxin lethal factor to the ADPribosylation domain of Pseudomonas exotoxin A are potent cytotoxins which are translocated to the cytosol of mammalian cells," The Journal of Biological Chemistry, vol. 267 (1992), pp. 15542-15548.
Arora et al., "Fusions of anthrax toxin lethal factor with shiga toxin and diphtheria toxin enzymatic domains are toxic to mammalian cells," Infect. Immun., vol. 62 (1994), pp. 4955-4961.
Heisler et al., "Actin-Directed Toxin. Acd toxin-produced actin oligomers poison form in controlled actin polymerization," Science, vol. 349 (2015), pp. 535-539.
Cordero et al., "The Actin cross-linking domain of the Vibrio cholerae RTX toxin directly catalyzes the covalent cross-linking of actin," The Journal of Biological Chemistry, vol. 281 (2006), pp. 32366-32374.
Kudryashov et al., "Characterization of the enzymatic activity of the actin cross-linking domain from the Vibrio cholerae MARTX Vc toxin," The Journal of Biological Chemistry, vol. 283 (2008), pp. 445-452.
Kudryashova et al., "Retrocyclins neutralize bacterial toxins by potentiating their unfolding," Biochem. Journal, vol. 467 (2015), pp. 311-320.
Pawlik et al., "Prodrug bioactivation and oncolysis of diffuse liver metastases by a herpes simplex virus 1 mutant that expresses the CYP2B1 transgene," Cancer, vol. 95 (2002), pp. 1171-1181.
Braidwood et al., "Antitumor activity of a selectively replication competent herpes simplex virus (HSV) with enzyme prodrug therapy," Anticancer Research, vol. 29 (2009), pp. 2159-2166.
Ishida et al., "Enhanced cytotoxicity with a novel system combining the paclitaxel-2'-ethylcarbonate prodrug and an HSV amplicon with an attenuated replication-competent virus, HF10 as a helper virus," Cancer Letters, vol. 288, (2010), pp. 17-27.
Shah et al., "Extein residues play an intimate role in the ratelimiting step of protein trans-splicing," Journal of the American Chemical Society, vol. 135 (2013), pp. 5839-5847.
Choe et al., "The crystal structure of diphtheria toxin," Nature, vol. 357 (1992), pp. 216-222.
Milne, Jill C., et al., "Protective antigen-binding domain of anthrax lethal factor mediates translocation of a heterologous protein fused to its amino- or carboxy-terminus," Molecular Microbiology, vol. 15 (1995), pp. 661-666.
Walavalkar et al., "Unique features of the anti-parallel, heterodimeric coiled-coil interaction between methyl-cytosine binding domain 2 (MBD2) homologues and GATA zinc finger domain containing 2A (GATAD2A/p66alpha)," The Journal of Biological Chemistry, vol. 288 (2013), pp. 3419-3427.
Kudryashova et al., "Targeting and inactivation of bacterial toxins by human defensins," Biological Chemistry, vol. 398 (2017), pp. 1069-1085.
Kudryashova et al., "Human defensins facilitate local unfolding of thermodynamically unstable regions of bacterial protein toxins," Immunity, vol. 41 (2014), pp. 709-721.
Fullner et al., "In vivo covalent cross-linking of cellular actin by the Vibrio cholerae RTX toxin," EMBO Journal, vol. 19 (2000), pp. 5315-5323.
Shah et la., "Naturally split inteins assemble through a "capture and collapse" mechanism," Journal of the American Chemical Society, vol. 135 (2013), pp. 18673-18681.
Wang et al., "Reduction of non-specific toxicity of immunotoxin by intein mediated reconstitution on target cells," International Immunopharmacology, vol. 66 (2019), pp. 288-295.
Riss et al., Cell Viability Assays in Assay Guidance Manual (eds G. S. Sittampalam et al.) (2004).
Alewine et al., "Efficacy of RG7787, a next-generation mesothelin-targeted immunotoxin, against triplenegative breast and gastric cancers," Molecular Cancer Therapeutics, vol. 13 (2014), pp. 2653-2661.
Tchou et al., "Mesothelin, a novel immunotherapy target for triple negative breast cancer," Breast Cancer Research and Treatment, vol. 133 (2012), pp. 799-804.
Hassan et al., "Major cancer regressions in mesothelioma after treatment with an anti-mesothelin immunotoxin and immune suppression," Science Translational Medicine, vol. 5 (2013).
Fukuhara et al., "Oncolytic virus therapy: A new era of cancer treatment at dawn," Cancer Sci., vol. 107 (2016), pp. 1373-1379.
Rehman et al., "Into the clinic: Talimogene laherparepvec (TVEC), a first-in-class intratumoral oncolytic viral therapy," Journal Immunotherapy Cancer, vol. 4 (2016), p. 53.
Yamamoto et al., "Imaging immediate-early and strictlate promoter activity during oncolytic herpes simplex virus type 1 infection and replication in tumors," Gene Therapy, vol. 13 (2006), pp. 1731-1736.
Onda et al., "An immunotoxin with greatly reduced immunogenicity by identification and removal of B cell epitopes," Proc. Natl. Acad. Sci. U S A, vol. 105 (2008), pp. 11311-11316.
Schmohl et al., "Mutagenic Deimmunization of Diphtheria Toxin for Use in Biologic Drug Development," Toxins (Basel) vol. 7 (2015), pp. 4067-4082.

(56) References Cited

OTHER PUBLICATIONS

Mazor et al., "Immunogenicity of therapeutic recombinant immunotoxins," Immunol. Rev., vol. 270 (2016), pp. 152-164.

Mazor et al., "Recombinant immunotoxin for cancer treatment with low immunogenicity by identification and silencing of human T-cell epitopes," Proc. Natl. Acad. Sci. U S A, vol. 111 (2014), pp. 8571-8576.

* cited by examiner

SPLIT-IMMUNOTOXINS FOR BOOSTING ONCOLYTIC VIRUS TOXICITY

CROSS-REFERENCE TO RELATED APPLICATIONS

This application is a National Stage of International Application No. PCT/US2019/019621, filed Feb. 26, 2019, which claims benefit of U.S. Provisional Application No. 62/635,073, filed Feb. 26, 2018, which is hereby incorporated herein by reference in its entirety.

BACKGROUND

Oncolytic viruses have emerged as a powerful tool in anti-cancer therapy. Similarly, the outstanding killing efficiency of bacterial toxins and their ability to selectively target cells has empowered their conversion to immunotoxins-anticancer drugs that have reached the level of clinical trials and FDA approved medications (FitzGerald, D. J., et al. Cancer Res. 2011 71:6300-6309; Haque, S. U., et al. Curr Opin Pharmacol. 2012 12:392-397; Robak, T. Future Oncol 2013 9:69-91). Yet, the broad application of both technologies is restricted by i) a scarcity of truly cancer-specific receptors for delivery of bacterial toxins to the cytoplasm of cancer cells and ii) low natural permissiveness of many tumors to clinically relevant oncolytic viruses. According to a recent study (Cuddington, B. P. & Mossman, K. L. J. Virol. 2014 88:6885-6895), human herpes simplex virus-1 (HSV-1), the only oncolytic virus currently approved for clinical applications in the US, is highly toxic to only ~10% of sixty representative human cancer cell lines from the standard NCI panel, another ~20% of cell lines show moderate to low response, and the virus is benign for the remaining ~70% of the cancer cell lines. A similar permissiveness was observed for other oncolytic viruses, including vaccinia (Cuddington, B. P. & Mossman, K. L. J. Virol. 2014 88:6885-6895) and measles vaccine (Noll, M. et al. Int J Oncol. 2013 43:103-112) viruses. There are non-permissive tumors even for strong oncolytic viruses (e.g., bovine herpes virus, 72% permissiveness), and yet the strong viruses would likely have to be attenuated to reduce their toxicity to normal cells.

SUMMARY

As disclosed herein, the assistance of a new generation of immunotoxins (split-immunotoxins) the range of cancers susceptible to elimination by oncolytic viruses and the specific toxicity of the latter can be expanded without compromising the selectivity of targeting. To accomplish this goal, a polypeptide chain of a potent bacterial toxin (e.g., a catalytic subunit of a Diphtheria toxin, DTA) can be split into two benign parts, which can then be delivered to the cytoplasm of cancer cells via two independent cancer-specific pathways: (1) together with an oncolytic virus (encoded in its genome); (2) as a split-immunotoxin delivered via receptor-specific toxin entry pathways (FIG. 1). The two parts are fused into a functional toxin only in the cytoplasm of dually targeted cancer cells by means of intein-catalyzed trans-splicing.

Therefore, disclosed herein is a first fusion protein that comprises a first split intein; a first extein that comprises a non-functional fragment of a toxin; and a ligand for receptor-mediated cell entry.

In some embodiments, the split intein is a C-intein, and the extein comprises the C-terminal fragment of the toxin. In other embodiments, the split intein is an N-intein, and the extein comprises the N-terminal fragment of the toxin.

Inteins are protein segments capable of excising themselves from a polypeptide and joining (splicing) the remaining (extein) parts with a peptide bond (Shah and Muir, 2013, Chem Sci. 2014; 5(1): 446-461). Any naturally or artificially split inteins can be used including (but not limited to) DnaE intein from *Synechocystis* sp. PCC6803 (SspDnaE) or DnaE intein from *Nostoc punctiforme* (NpuDnaE).

Any peptide toxic to cells, such as cancer cells, can be used as the toxin (i.e., split extein) so long as it can be separated into two non-functional fragments and spliced back together by intein-catalyzed trans-splicing. The groups of applicable toxins may include ribotoxins, apoptosis and pyroptosis inducing toxins, toxins causing necrosis, as well as genotoxins (e.g., cytolethal distending toxins (CDT)). For example, in some embodiments, the ribotoxin is a diphtheria toxin from *Corynebacterium diphtheria* (GenBank: AOU74567.1). In some embodiments the ribotoxin is a shiga toxin of *Shigella dysinteriae* or entherophatogenic strains of *Escherichia coli* (GenBank: CAC05622.1). In some embodiments the toxin is a *Pseudomonas aeruginosa* exotoxin A (GenBank: KGB89250.1). In other embodiments the ribotoxin is a plant toxins gelonin from *Gelonium multiflorum* (GenBank: AAB47013.1). In some embodiments the ribotoxin is a ricin from *Ricinus communis* (NCBI Reference Sequence: NP_001310630.1). In some embodiments the apoptosis causing toxin is the effector domain of *Photorhabdus luminescence* Mcf1 toxin (GenBank: AF503504.2). In some embodiments apoptosis can be induced by the catalytic domain of *Clostridium difficile* TcdB toxin (GenBank: HG002394.1). The pyroptosis inducing toxins can be various Rho-GTPase modifying toxins such as *Vibrio parahemolyticus* VopS toxin (GenBank:), and *Clostridium botulinum* C3 toxin (GenBank: AAA23212.1), catalytic subunit of *Bordetella pertussis* toxin (PT) (GenBank: ALI23783.1). In some embodiments the cytolethal distending toxin is SdtB subunit of CDT toxin of *Shigella dysentheriae* (GenBank: OOO89703.1) or *Helicobacter* spp. (GenBank: PZT48983.1).

These and other toxins may not kill the targeted cancer cells directly, but they are expected to stimulate the immune response leading to elimination of the cancer by the patient immune system. Other potent natural proteinaceous toxins can be adopted for use in the disclosed compositions and methods.

The ligand can be any peptide sequences that either bind a receptor on the target cell, or bind an adapter protein that binds a receptor on the target cell, and in so doing results in receptor-mediated entry into the cell. For example, anthrax toxin (Atx) entry pathway can be modified to selectively recognize specific receptors abundant on cancer cells. Therefore, in some cases, the ligand comprises the N-terminal fragment of anthrax Lethal Factor ($LF_N$), which binds to the pore-forming Protective Antigen (PA) Atx subunit, which can be targeted to a specific receptor. In some cases, the ligand is any toxin delivery component enabling an entry of the polypeptide toxin into a human cell via a receptor mediated entry pathway.

In some embodiments, the fusion protein has the formula:

$NH_3$-$Ext_N$-$Int_N$-Lig-COOH, or $NH_3$-Lig-$Ext_N$-$Int_N$-COOH, wherein "$Ext_N$" comprises the N-terminal fragment of a toxin, wherein "$Int_N$" comprises a N-intein, wherein "Lig" comprises a ligand configured for receptor-mediated cell entry, and wherein "-" comprises a linker or peptide bond.

In some embodiments, the fusion protein has the formula:

$NH_3$-$Int_C$-$Ext_C$-Lig-COOH, or $NH_3$-Lig-$Int_C$-$Ext_C$-COOH, wherein "$Ext_C$" comprises the C-terminal fragment of a toxin, wherein "$Int_C$" comprises a C-intein, wherein "Lig" comprises a ligand configured for receptor-mediated cell entry, and wherein "-" comprises a linker or peptide bond.

Also disclosed is a recombinant viral vector that comprises a nucleic acid sequence encoding a second fusion protein comprising a second split intein, and a second extein that comprises a non-functional fragment of a toxin. As will be appreciated by one of ordinary skill in the art, the toxin fragment of the first fusion protein and the second fusion protein should form a functional toxin upon intein-catalyzed trans-splicing.

In some embodiments, the split intein is an N-intein, and the second extein comprises the N-terminal fragment of the toxin. In other embodiments, the split intein is a C-intein, and the second extein comprises the C-terminal fragment of the toxin.

Also disclosed is a viral particle, comprising an oncolytic virus encapsulating a viral vector disclosed herein. In some embodiments, the wherein oncolytic virus comprises an adenovirus, reovirus, VSV, NDV, HSV, BSV, or vaccinia virus. For example, in some embodiments, the oncovirus is an HSV-Q Virus.

Also disclosed is a system, comprising a first fusion protein disclosed herein and a viral particle comprising a recombinant viral vector disclosed herein, wherein co-localization of the split intein of the fusion protein and the split intein encoded by the viral vector in a cell results in trans-splicing of the first extein and the second extein to form a functional toxin in the cell.

In some embodiments, the ligand comprises the N-terminal fragment of anthrax Lethal Factor ($LF_N$). Therefore, in some embodiments, the system further comprises a pore-forming protective antigen (PA) subunit of anthrax toxin (a mutated receptor recognition-deficient form of PA) fused to a heterologous, receptor-binding moiety specific for a target receptor. Examples of the receptor-targeting ligands include, but are not limited to, the epidermal growth factor (EGF), affibody specific for the HER2 receptor, and an anti-mesothelin Fv antibody. In other embodiments, delivery systems of pseudomonas toxin, shiga toxin, cholera toxin, and diphtheria toxins can be utilized.

The receptor being targeted by the disclosed system can be on any desired cell. In some cases, the receptor is a cancer-specific receptor. For example, the receptor can be selected from the group comprising TEM8, EGFR, HER2, mesothelin, and TAG-72.

Also disclosed is a method for treating cancer in a subject, comprising administering to the subject a first composition comprising a fusion protein disclosed herein, and a second composition comprising a viral particle disclosed herein, wherein collocation of the split intein of the fusion protein and the split intein encoded by the viral vector in a cancer cell results in trans-splicing of the exteins to form a functional toxin in the cancer cell, thereby treating the cancer.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows diphtheria toxin effector domain (DTA) split at five positions optimized for efficient trans-splicing and domain integrity and fused to i) Anthrax Toxin (Atx) delivery domain ($LF_N$) and ii) split-intein domains ($DnaE_N$ and $DnaE_C$). Short coiled-coil regions (CC) are added to improve affinity of the split-inteins and enable trans-splicing under in vivo conditions. FIG. 2B shows that all five split-DTA toxin pairs are soluble and upon in vitro trans-splicing reconstitute an active toxin that crosses the membrane and kills cells. FIG. 2C shows that ACD toxin of *Vibrio cholerae* loses its activity upon splitting and regains it after in vitro trans-splicing. Full-length wild type (wt-) ACD toxin covalently crosslinks actin into arrays of oligomers (left lane), but loses this ability upon splitting at three sites (central lanes). Incubation of the matching N- and C-split-toxin pairs flanked with N-($I_N$) and C-parts ($I_C$) of DnaE split intein, respectively, results in a regain of the toxin's functional activity in two out of three cases tested (the last three lanes). Importantly, the $LF_N$ sequence fused N-terminally to all C-terminal split-toxins did not hamper the trans-splicing. The actin crosslinking activity of ACD is revealed via appearance on the SDS-gel of covalent actin oligomers (indicated as A1-A5) of higher molecular weight.

FIG. 4A shows split-DTA toxin potently poisons U2OS cells upon expression of one and trans-membrane delivery of another split-components. Stably transfected cells expressing EGFP-$DTA_N$-$DnaE_N$ have been treated with various doses of PA/$LF_N$-$DnaE_C$-$DTA_C$. Potent inhibition of protein synthesis (determined by SUnSET method) and related toxicity was observed upon treating the cells with as little as 10 pM of $LF_N$-$DnaE_C$-$DTA_C$. Full-length active toxin ($LF_N$-FL-DTA) is shown as a control. FIG. 4B shows split-DTA toxin potently poisons SK-BR3 breast cancer cells upon expression of one and trans-membrane delivery of another split-components. Stably transfected cells expressing EGFP-$DTA_N$-$DnaE_N$ have been treated with various doses $LF_N$-$DnaE_C$-$DTA_C$ and $PA_{zHER2}$-Protective Antigen (PA) modified for delivery via HER2 surface receptors.

Potent inhibition of protein synthesis (determined by SUnSET method) and related toxicity was observed upon treating the cells with 100 pM of $LF_N$-$DnaE_C$-$DTA_C$. Full-length active toxin ($PA_{zHER2}$/LFN-FL-DTA) is shown as a control.

Figure 4A:
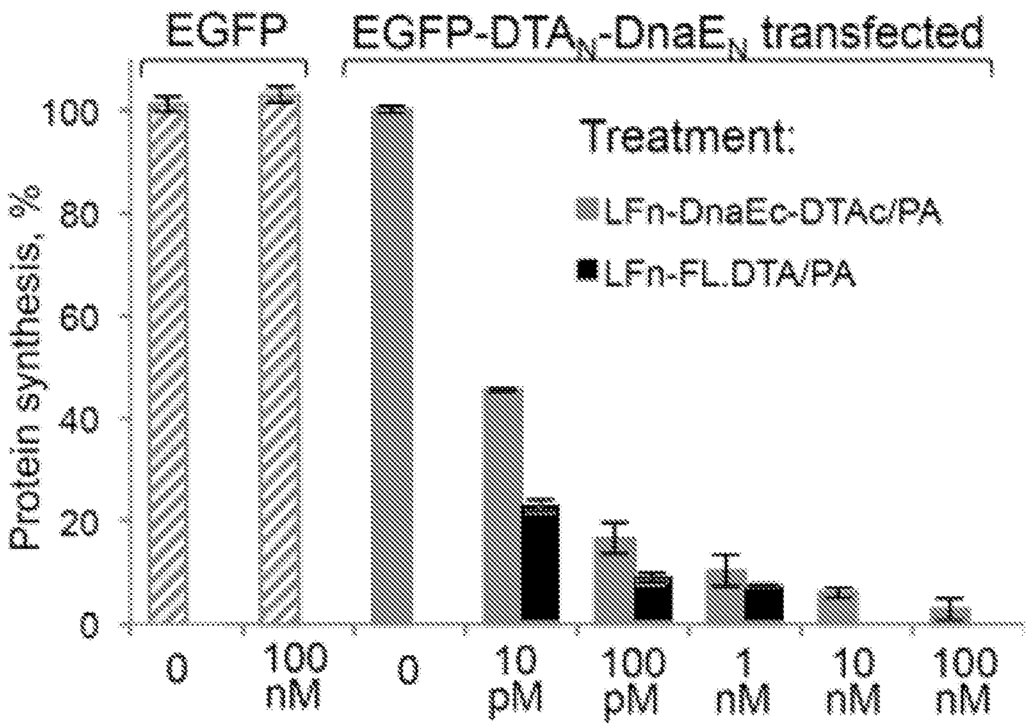
FIGS. 4A, 4B, 4C, and 4D demonstrate reconstitution of active full-length DTA inside the cells expressing EGFP-$DTA_N$-$DnaE_N$ upon delivery of a complementary PA/$LF_N$-$DnaE_C$-$DTA_C$ split-toxin pair through specific cell-surface receptors.
Figure 4B:
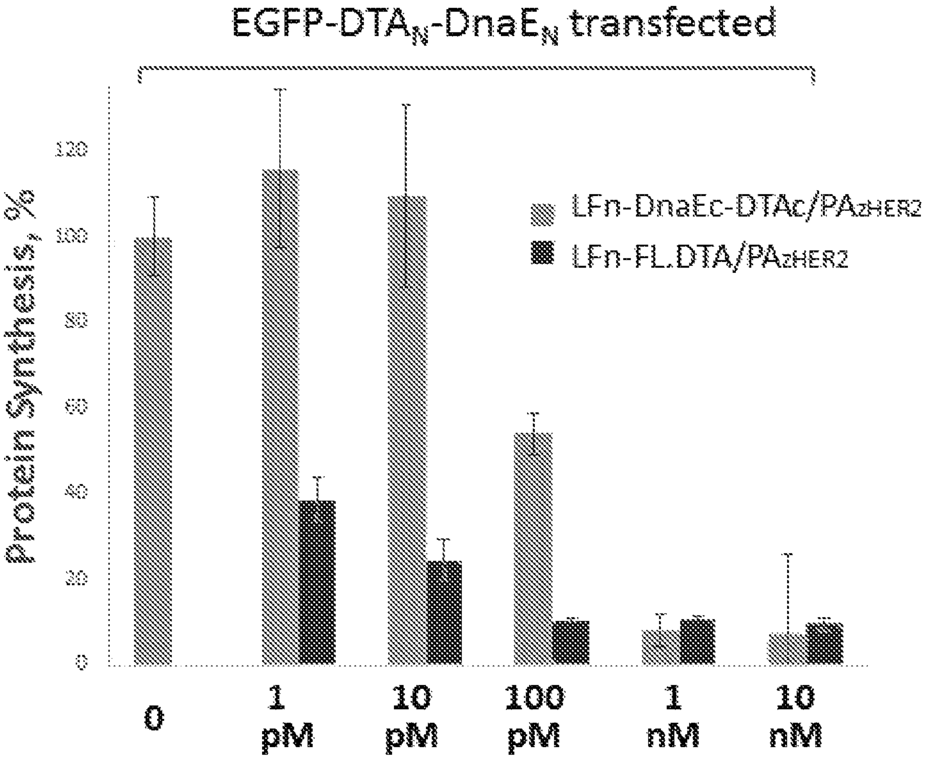
Figure 4C:
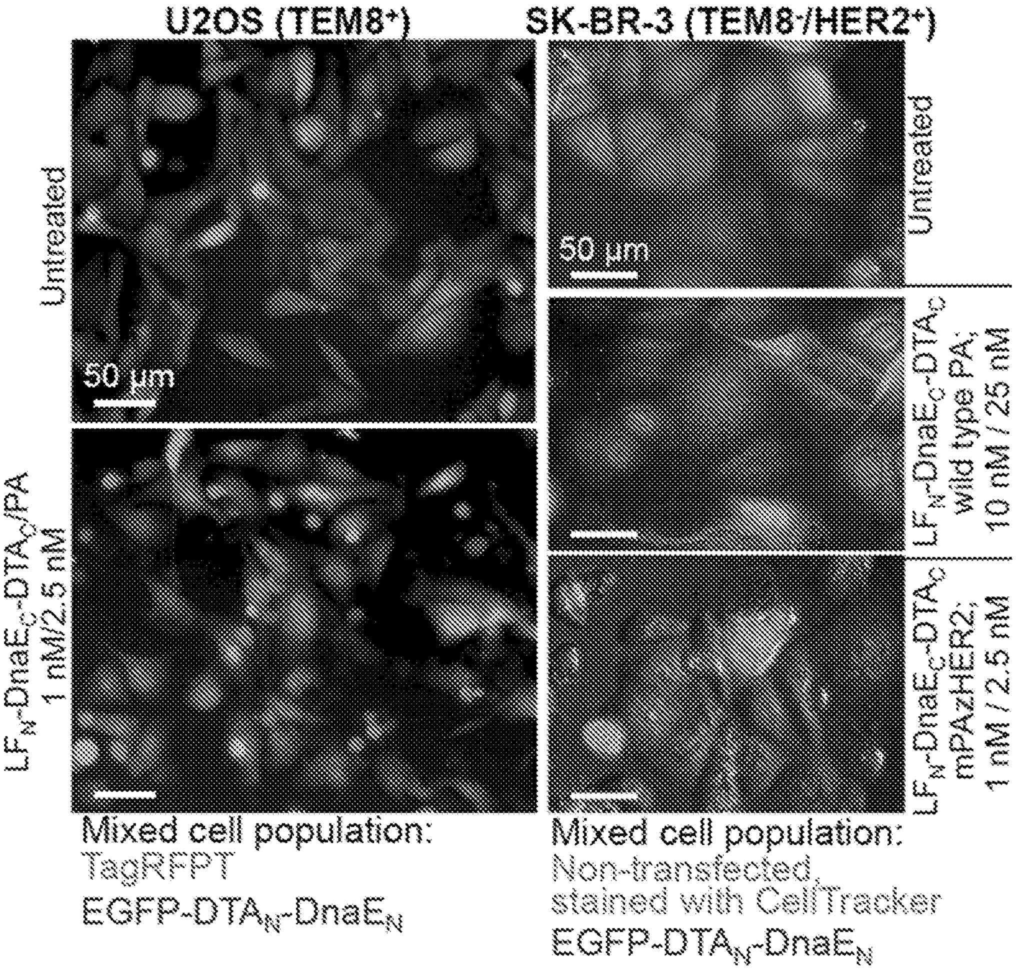
Figure 4D:
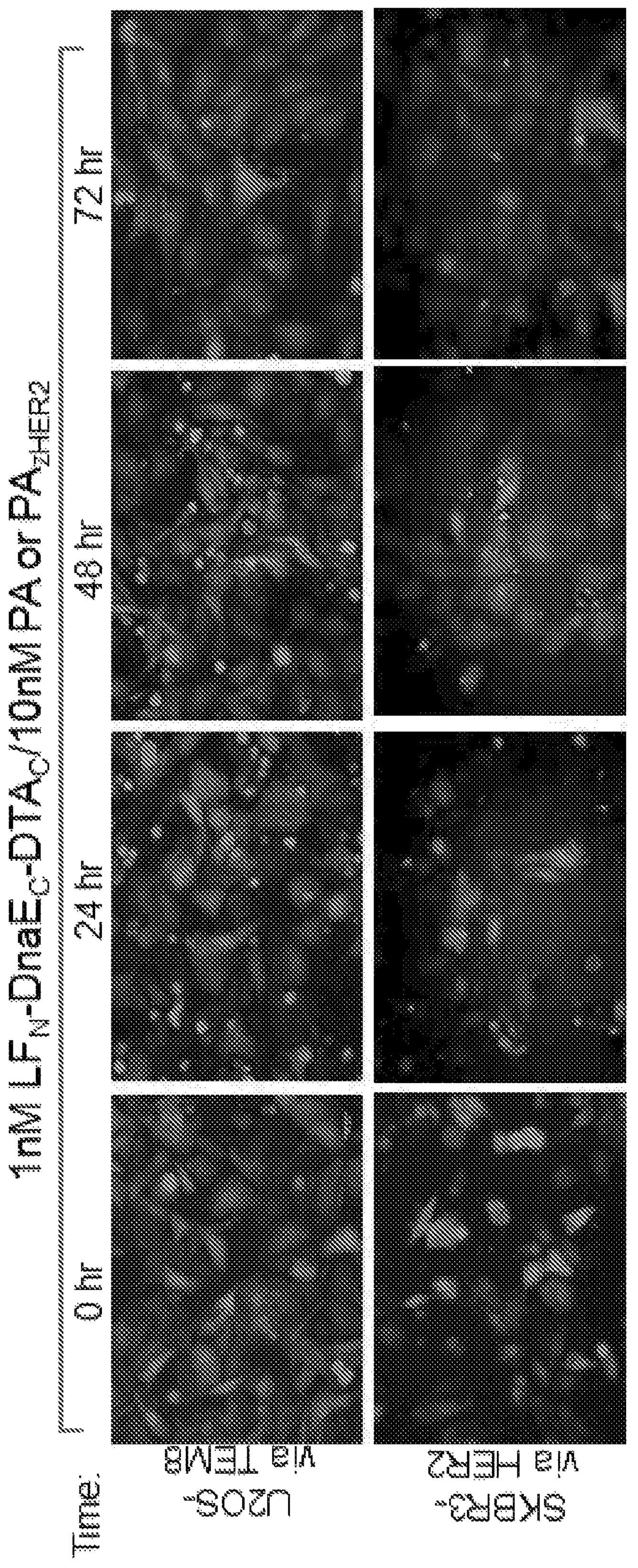

FIG. 4C shows split-DTA toxin potently poisons U2OS and SK-BR-3 cells upon individual delivery of the split-components. Transfected cells expressing the EFGP-$DTA_N$-$DnaE_N$ part of split-DTA, but not control cells, were poisoned upon receptor-mediated delivery of the second split-component—$LF_N$-$DnaE_C$-$DTA_C$. The selectivity towards U2OS or SK-BR-3 cells was achieved by specificity of the delivery subunit, PA or mPAzHER2, targeting TEM8 or HER2 receptors, respectively. While 1 nM concentration of $LF_N$-$DnaE_C$-$DTA_C$/PA was sufficient to kill U2OS cells (left bottom panel), 10-fold higher doses were benign to SK-BR-3 cells missing the TEM8 receptor (right middle panel). FIG. 4D shows that transfected cells expressing the EFGP-$DTA_N$-$DnaE_N$ part of split-DTA (green cells), but not control cells (transfected by red fluorescent protein mCherry (U2OS cells; top panel) or stained with a blue cell permeable dye (SK-BR-3 cells; lower panel), were poisoned upon receptor-mediated delivery of the second split-component—$LF_N$-$DnaE_C$-$DTA_C$. The selectivity towards U2OS or SK-BR-3 cells was achieved by specificity of the delivery subunit, PA or mPAzHER2, targeting TEM8 or HER2 receptors, respectively. 1 nM concentration of $LF_N$-$DnaE_C$-$DTA_C$/PA or $LF_N$-$DnaE_C$-$DTA_C$/$PA_{zHER2}$ was sufficient to kill U2OS cells or SK-BR-3 cells, respectively.

Figure 5:
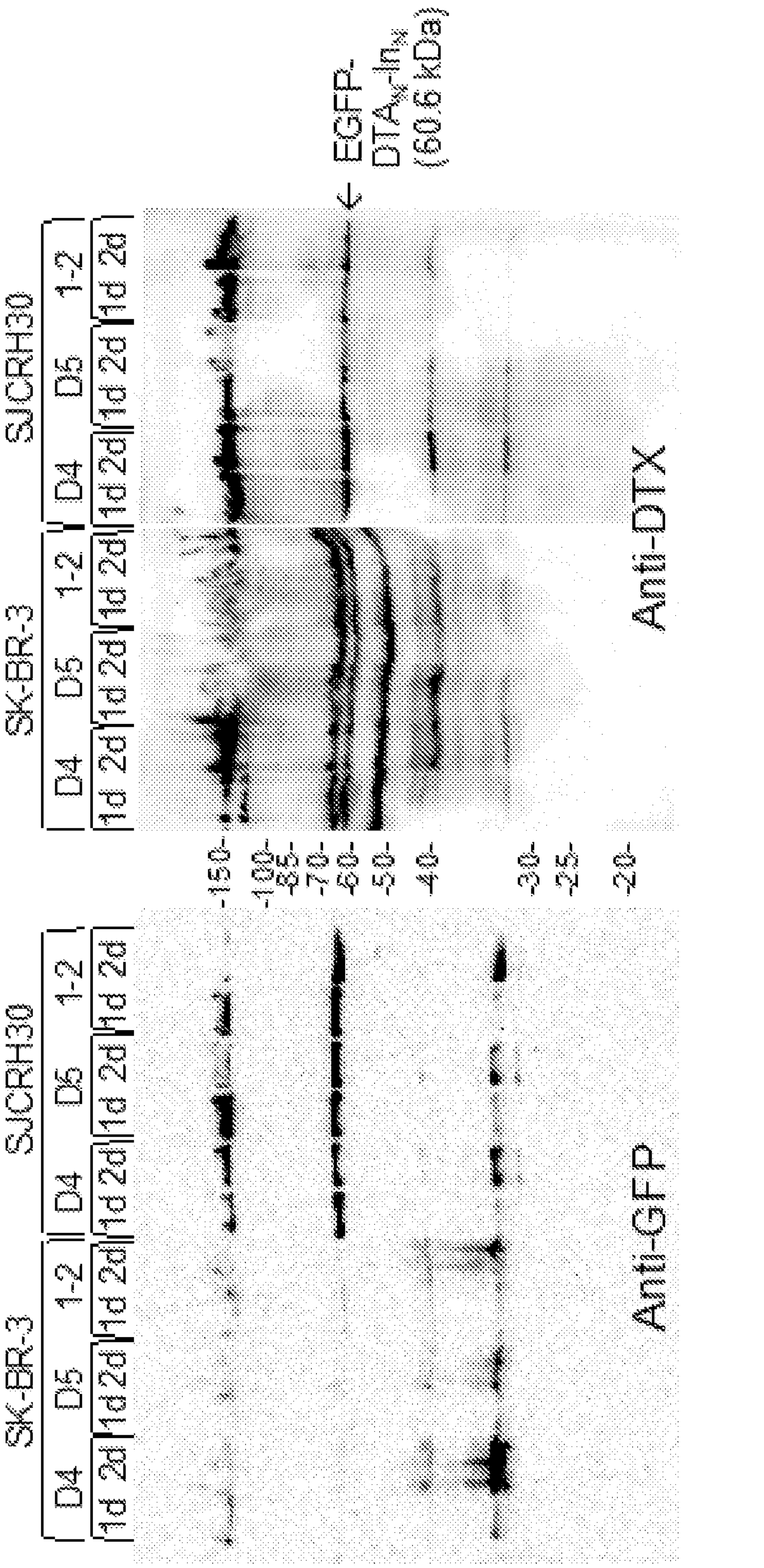

FIG. 5 depicts anti-GFP and anti-diphtheria toxin (DTX) Western blots to verify EGFP-$DTA_N$-$DnaE_N$-$DnaE_N$ expression in SK-BR-3 and SJCRH30 cell lines infected with three clones of recombinant oncolytic HSV-Q virus encoding the N-terminal part of the split DTA toxin HSV-EGFP-$DTA_N$-$DnaE_N$ (clones D4, D5, and 1-2) following 1 and 2 days post-infection (1d and 2d, respectively).

Figure 6B:
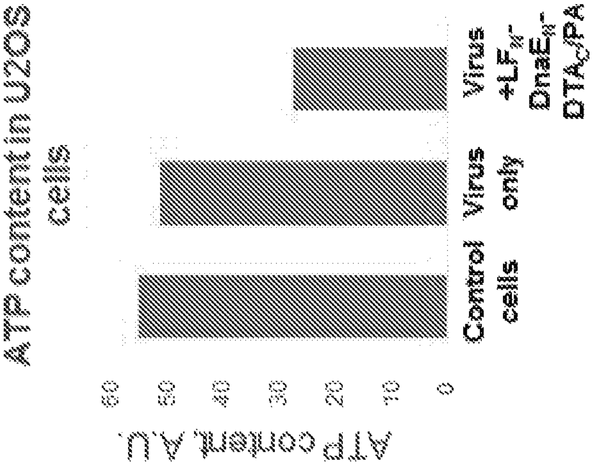
Figure 6A:
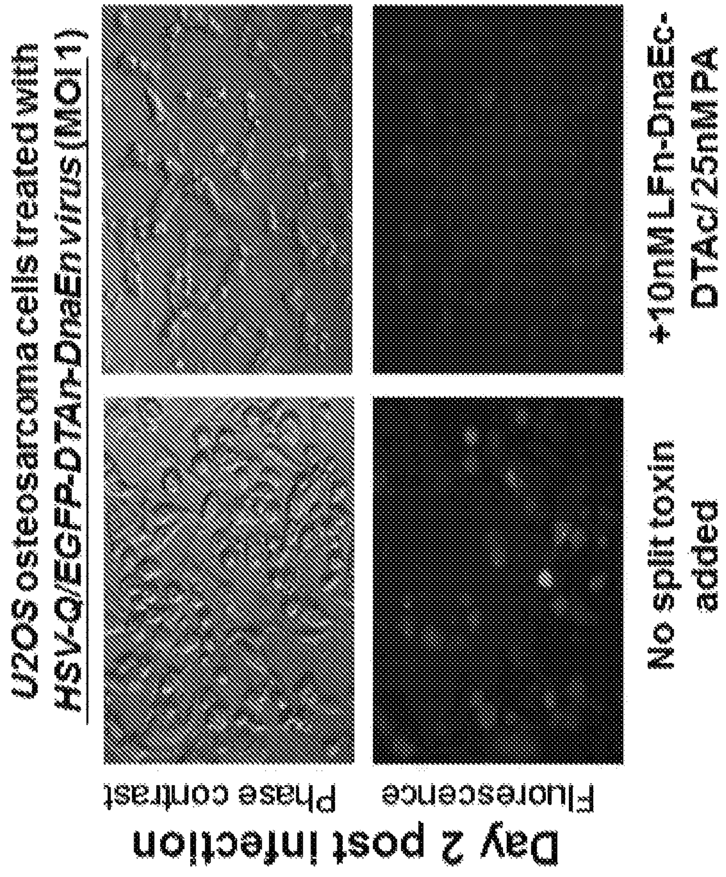
Figure 6C:
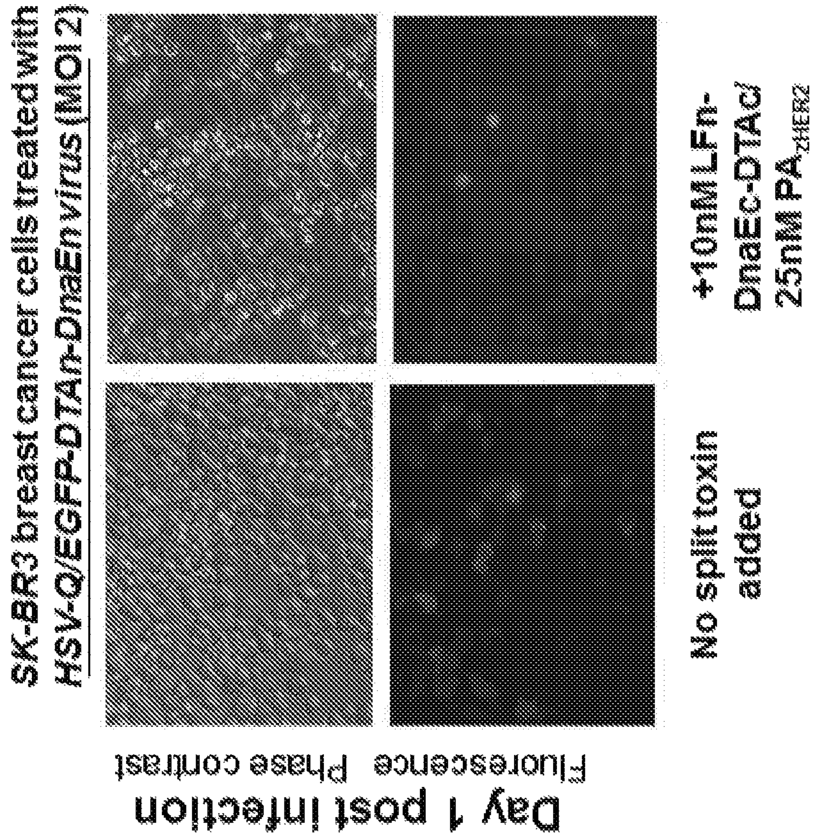
Figure 6D:

FIGS. 6A, 6B, 6C, and 6D show U2OS and SK-BR-3 cells treated via a dual action of oncolytic HSV-Q virus encoding the N-terminal part of the split DTA toxin and the C-terminal toxin part delivered as a protein. On FIGS. 6A and 6C (FIG. 6A: U2OS cells and FIG. 6C: SK-BR-3 cells) a panel of human cancer cell lines were infected at different MOI with the HSV-Q virus encoding the EGFP-$DTA_N$-$DnaE_N$ toxin. Expression of the EGFP fused split-toxin component in all tested cancer cell lines was evident from the characteristic green fluorescence and subsequent cell rounding, albeit the fraction of affected cells and time to rounding varied depending on MOI and the cell type. FIGS. 6B and 6D show that addition of the corresponding $LF_N$-$DnaE_C$-$DTA_C$ toxin (10 nM) along with a modified PA (25 nM) three to five hours after the infection caused notable decrease in the production of EGFP-$DTA_N$-$DnaE_N$ (quantified on FIG. 7) owing to inhibition of protein synthesis. Cell toxicity was measured by the ATP level (FIG. 6B: U2OS cells) or by monitoring a reducing potential (FIG. 6D: SK-BR-3 cells). To avoid interference with the virus propagation, use of toxins acting via mechanisms independent of protein synthesis inhibition will be explored.

Figure 7:
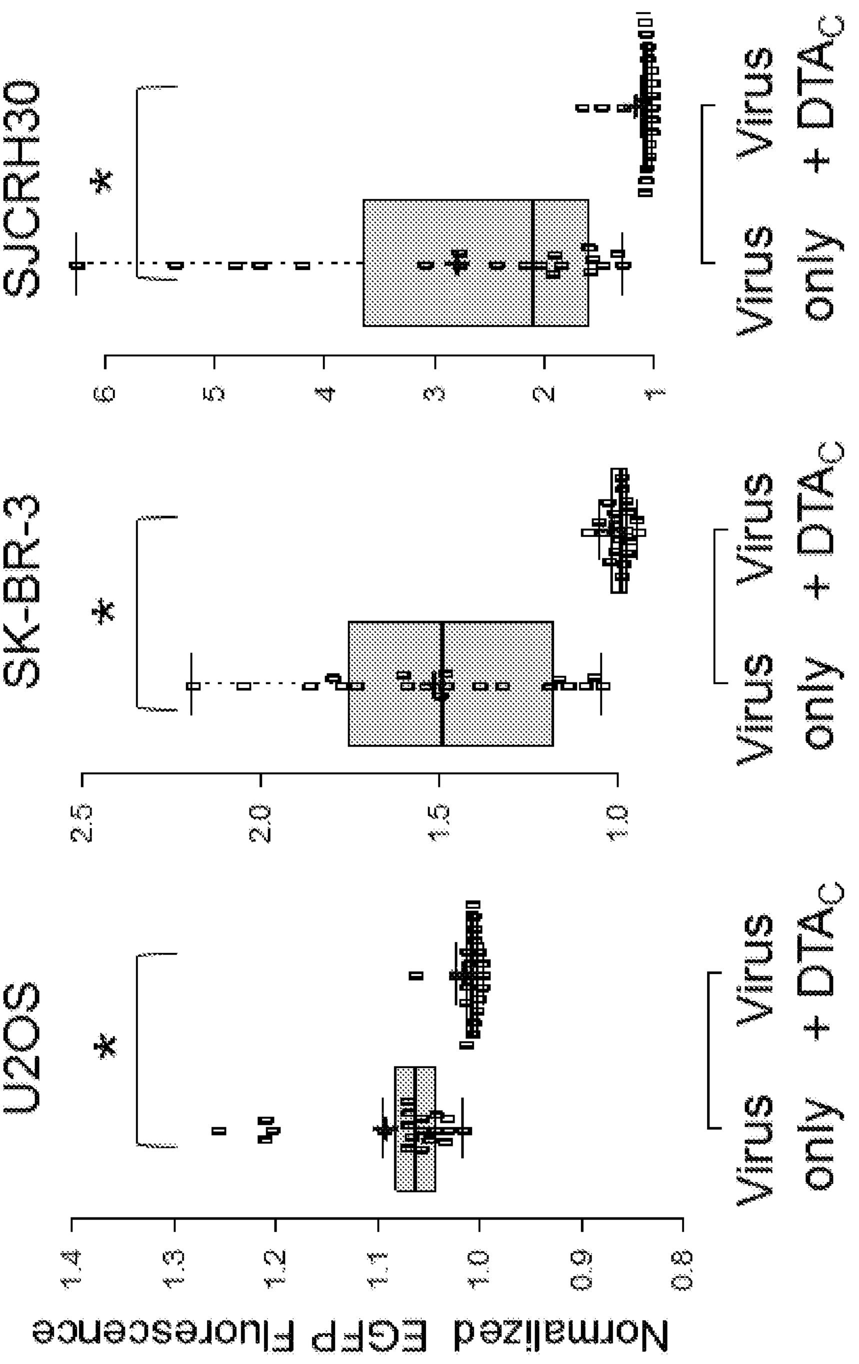

FIG. 7 shows Inhibition of EGFP synthesis by a trans-spliced DTA toxin upon its reconstitution in cancer cells from two fragments delivered via transduction of HSV-Q virus (the EGFP-Split-$DTA_N$-$DnaE_N$ fragment) followed by trans-membrane delivery of $LF_N$-$DTA_C$-$DnaE_C$/PA added to the medium 3-5 hours post-transduction. EGFP signal in cells quantified based on the level of fluorescence intensity 1 day post-treatment.

DETAILED DESCRIPTION

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "peptide," "protein," and "polypeptide" are used interchangeably to refer to a natural or synthetic molecule comprising two or more amino acids linked by the carboxyl group of one amino acid to the alpha amino group of another.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

A "ligand", as used herein, refers generally to all molecules capable of reacting with or otherwise recognizing or binding to a receptor on a cell, or an adapter protein that binds a receptor on the cell.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. A "spacer", as used herein, refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule. Especially in the case where the linkers enable protein purification, linkers in protein or peptide fusions are sometimes engineered with cleavage sites for proteases or chemical agents, which enable the liberation of the two separate proteins. This technique is often used for identification and purification of proteins, by fusing a GST protein, FLAG peptide, or a hexa-his peptide (aka: a 6×His-tag) which can be isolated using nickel or cobalt resins (affinity chromatography).

Alternatively, internal ribosome entry sites (IRES) elements can be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages.

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors, which serve equivalent functions.

In order to express a polypeptide or functional nucleic acid, the nucleotide coding sequence may be inserted into appropriate expression vector. Methods to construct expression vectors containing genetic sequences and appropriate transcriptional and translational control elements are well known in the art. These methods include in vitro recombinant DNA techniques, synthetic techniques, and in vivo genetic recombination. Such techniques are described in Sambrook et al., Molecular Cloning, A Laboratory Manual (Cold Spring Harbor Press, Plainview, N.Y., 1989), and Ausubel et al., Current Protocols in Molecular Biology (John Wiley & Sons, New York, N.Y., 1989).

Expression vectors generally contain regulatory sequences necessary elements for the translation and/or transcription of the inserted coding sequence. For example, the coding sequence is preferably operably linked to a promoter and/or enhancer to help control the expression of the desired gene product.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity.

A "promoter" is generally a sequence or sequences of DNA that function when in a relatively fixed location in regard to the transcription start site. A "promoter" contains core elements required for basic interaction of RNA polymerase and transcription factors and can contain upstream elements and response elements.

An "endogenous" enhancer/promoter is one, which is naturally linked with a given gene in the genome. An "exogenous" or "heterologous" enhancer/promoter is one, which is placed in juxtaposition to a gene by means of genetic manipulation (i.e., molecular biological techniques) such that transcription of that gene is directed by the linked enhancer/promoter.

Promoters used in biotechnology are of different types according to the intended type of control of gene expression. They can be generally divided into constitutive promoters, tissue-specific or development-stage-specific promoters, inducible promoters, and synthetic promoters.

Constitutive promoters direct expression in virtually all tissues and are largely, if not entirely, independent of environmental and developmental factors. As their expression is normally not conditioned by endogenous factors, constitutive promoters are usually active across species and even across kingdoms.

Tissue-specific or development-stage-specific promoters direct the expression of a gene in specific tissue(s) or at certain stages of development. For plants, promoter elements that are expressed or affect the expression of genes in the vascular system, photosynthetic tissues, tubers, roots and other vegetative organs, or seeds and other reproductive organs can be found in heterologous systems (e.g. distantly related species or even other kingdoms) but the most specificity is generally achieved with homologous promoters (i.e. from the same species, genus or family). This is probably because the coordinate expression of transcription factors is necessary for regulation of the promoter's activity.

The performance of inducible promoters is not conditioned to endogenous factors but to environmental conditions and external stimuli that can be artificially controlled. Within this group, there are promoters modulated by abiotic factors such as light, oxygen levels, heat, cold and wounding. Since some of these factors are difficult to control outside an experimental setting, promoters that respond to chemical compounds, not found naturally in the organism of interest, are of particular interest. Along those lines, promoters that respond to antibiotics, copper, alcohol, steroids, and herbicides, among other compounds, have been adapted and refined to allow the induction of gene activity at will and independently of other biotic or abiotic factors.

An enhancer is a sequence of DNA that functions at no fixed distance from the transcription start site and can be either 5' or 3' to the transcription unit. Furthermore, enhancers can be within the coding sequence itself. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time, A preferred promoter of this type is the CMV promoter (650 bp). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

In some embodiments the vector is derived from either a virus or a retrovirus. Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

In the context of an oncolytic HSV, an immediate early IE4/5 promoter (acts immediately post viral infection) and strict late gC or UL38p promoters associated with viral replication (act late in the replication cycle) can be used for tumor-selective gene expression of the recombinant constructs.

The compositions disclosed can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products.

A number of embodiments of the invention have been described. Nevertheless, it will be understood that various modifications may be made without departing from the spirit and scope of the invention. Accordingly, other embodiments are within the scope of the following claims.

EXAMPLES

Integration of a gene encoding a potent bacterial toxin into oncolytic viruses could extend the panel of targetable tumors, but is hindered by several factors. First, many exceptionally potent bacterial toxins are expected to hamper replication of the virus (e.g. by inhibiting protein synthesis) and thus diminish its therapeutic potential, emphasizing the importance of a precise temporal control over the toxin production. Second, enforcing a virus with a toxin DNA may lead to an unintentional creation of a novel infectious agent with unpredictable properties, raising a concern of safety.

Figure 1:
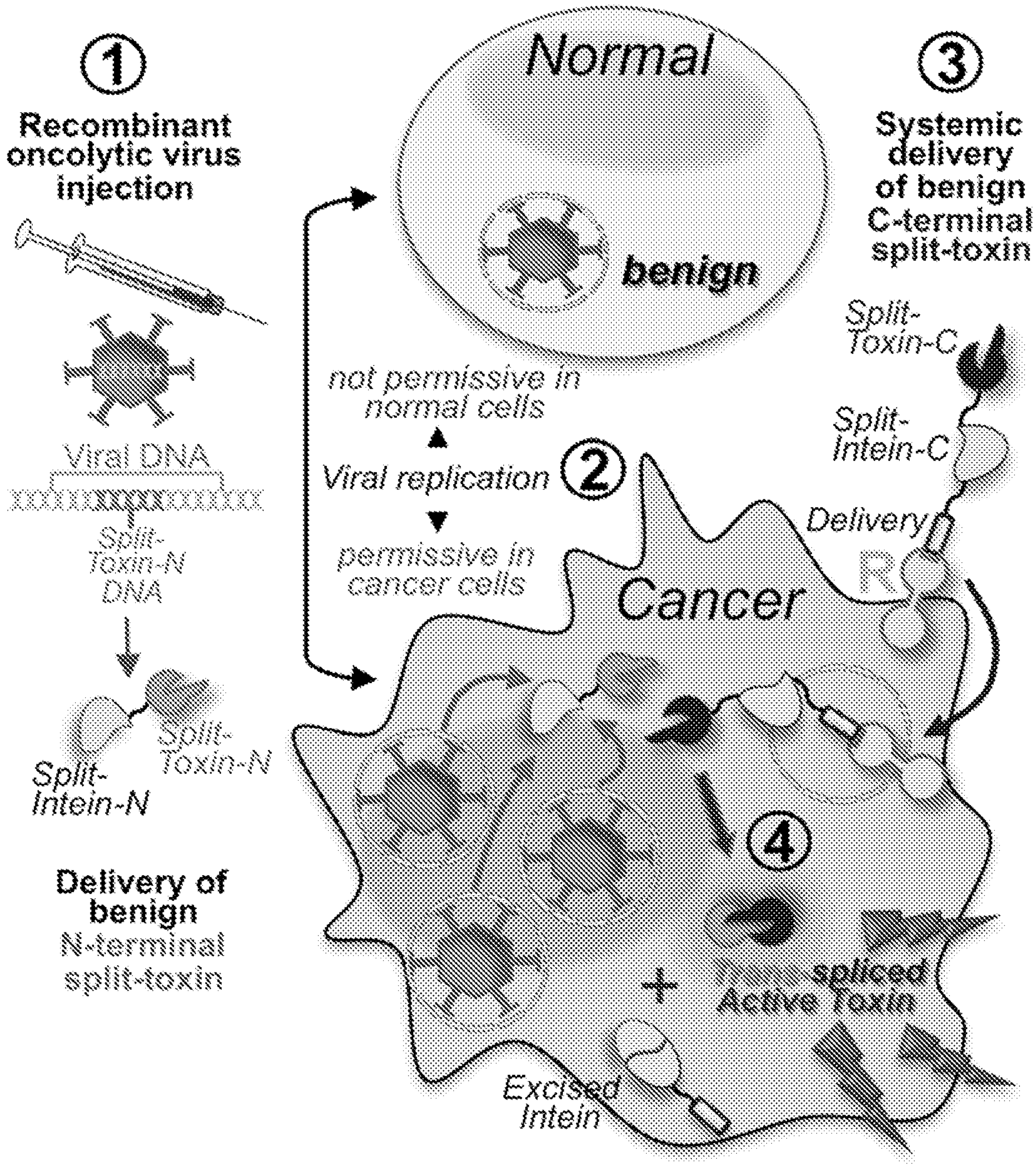
FIG. 1 illustrates one embodiment of the use of split-immunotoxins to boost oncolytic virus toxicity. A catalytic subunit of a potent toxin is split into two benign parts (Split Toxin-N and -C), which are fused to corresponding split-intein parts (Split Intein-N and -C) and a toxin delivery component. The N-terminal construct is delivered into the cytoplasm of targeted cells via a recombinant oncolytic virus (1), replication of which is restricted to cancer cells (2). The C-terminal construct is delivered via a cancer-specific receptor (R)-mediated pathway (3). Fully functional toxin is reconstituted via intern-catalyzed trans-splicing only in the cytoplasm of cancer cells (4).

To overcome these limitations, a new approach was evaluated based on the phenomenon of split-intein-based trans-splicing. The new approach involves splitting a potent bacterial toxin (DTA) into two benign, enzymatically inactive parts, flanking these parts with split-intein sequences, and delivering them to the cytoplasm of cancer cells via two independent pathways: one part embedded in the genome of an oncolytic virus, while the second part is delivered as a protein via one of the receptor-mediated delivery pathways enriched on the surface of cancer cells (FIG. 1). Such approach reaches three goals: (1) it increases the range of targeting by affecting cells that permit replication of oncolytic virus at low levels; (2) it increases the specificity of targeting as both pathways are cancer-specific; (3) since the resulting recombinant virus contains only DNA for a benign toxin part, this precludes the escape of the virus with the full-length toxin-encoding DNA. It can be noticed that the proposed innovative approach is reminiscent to those using viruses for expression of pro-drug activators (Pawlik, T. M., et al. Cancer 2002 95:1171-1181; Braidwood, L., et al. Anticancer Res 2009 29:2159-2166; Ishida, D., et al. Cancer Lett 2010 288:17-27); except that it offers higher specific toxicity towards cancer cells owing to exceptional potency of bacterial toxins, while simultaneously providing much lower side toxicity due to the cancer-selective receptor-mediated delivery of the split-toxin.

Example 1: Identifying Effective Split-Positions on the Catalytic Subunit of Diphtheria Toxin

Experimental Design

Figure 2A:
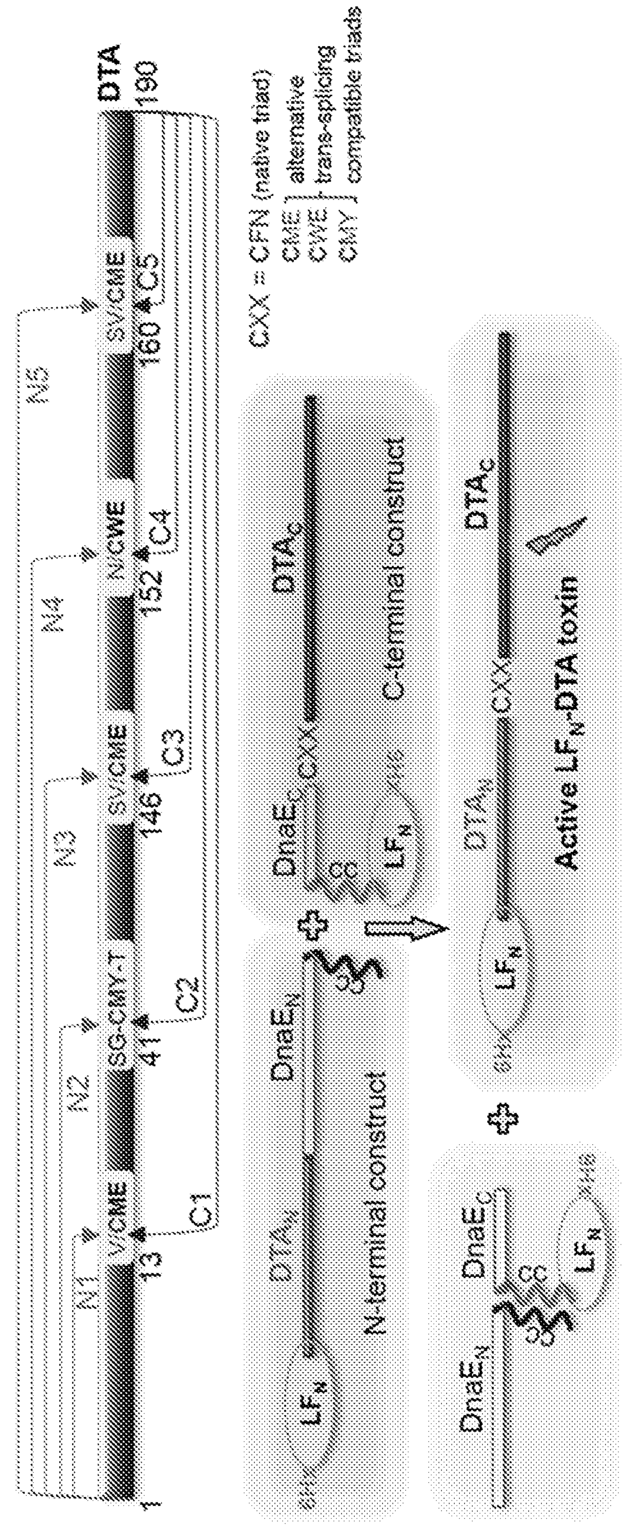
FIGS. 2A, 2B, and 2C show intern-based trans-splicing of diphtheria and ACD toxins.

Splitting and reassembly of the fully functional toxin may lead to several potential hurdles. First, trans-splicing is sensitive to the C-extein residues at the splitting site (naturally occurring CFN for $DnaE_{Npu}$; (Shah, N. H., et al. J Am Chem Soc. 2013 135:5839-5847)). Therefore, for trans-splicing to occur, either the CFN triad or other residues supporting the catalysis (e.g., CML, CMY, CWE, CWN, CWL; (Cheriyan, M., et al. J Biol Chem. 2013 288:6202-6211)) must be inserted into the toxin at the split-site, or toxin's own residues must be mutated to such sequences. A particular triad is selected to reproduce as closely as possible the original toxin sequence (FIG. 2A). Furthermore, to solve this challenge and ensure that such mutations do not interfere with the enzymatic properties of the toxin, the splitting sites are selected at the toxin's flexible loops, areas naturally more tolerant to mutational interventions than conserved secondary structure elements. Importantly, loop areas also provide more flexibility for unobstructed interaction between the intein parts, which is essential for their proper orientation in catalysis. The second potential hurdle that can be expected upon toxin splitting is low solubility of the resulted constructs due to exposed hydrophobic residues and incorrect folding. This problem is addressed by splitting at the loops separating toxin domains with minimal surface contacts. Solubility can be increased, when necessary, by replacing selected nonpolar amino acids at the surfaces disrupted by splitting or elsewhere with polar ones. Intracellular delivery of the constructs is achieved by utilizing the Atx delivery machinery (Arora, N., et al. J Biol Chem. 1992 267:15542-15548; Arora, N. & Leppla, S. H. Infect Immun 1994 62:4955-4961; Heisler, D. B., et al. Science 2015

349:535-539) (i.e., a fusion of the $LF_N$ with the split-DTA constructs and mixing with the pore-forming PA subunit retargeted to receptors enriched in cancers (Chen, K. H., et al. J Biol Chem. 2007 282:9834-9845; McCluskey, A. J., et al. Mol Oncol. 2013 7:440-451; Mechaly, A., et al. MBio. 2012 3(3)).

Results

Figure 2B:
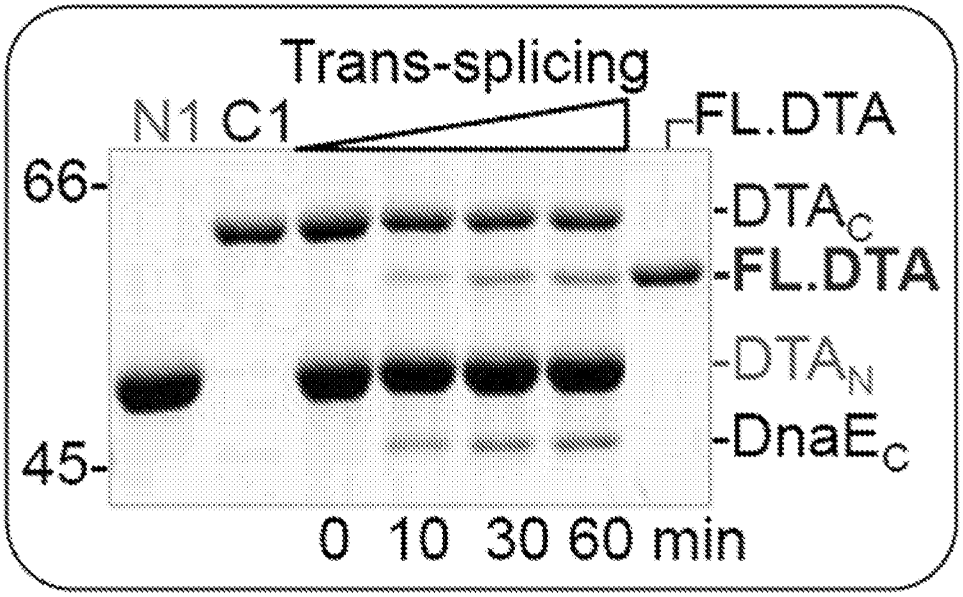

With the above considerations in mind, five split-sites were designed on DTA toxin as indicated in FIG. 2A, all five pairs of constructs were expressed in *E. coli*, purified, and the efficiency of their trans-splicing in a test tube tested (FIG. 2B). In each case, 20 to 30% efficiency of trans-splicing was observed. Importantly, all five reconstituted full-length toxins demonstrated potent toxicity upon their delivery to the cytoplasm of various tested human cell lines (e.g., HeLa, U2OS, SK-BR-3) using the Atx delivery machinery. Of the five constructs, only the C-terminal part of the first pair demonstrated some level of toxicity. This pair of the split-toxin was eliminated from further considerations. Four other pairs did not show any toxicity as individual split-constructs, but regained the activity upon in vitro trans-splicing.

Therefore, a potent bacterial toxin can be split into two inactive parts, which can regain the activity upon their intein-mediated reconstitution in vitro.

Figure 2C:
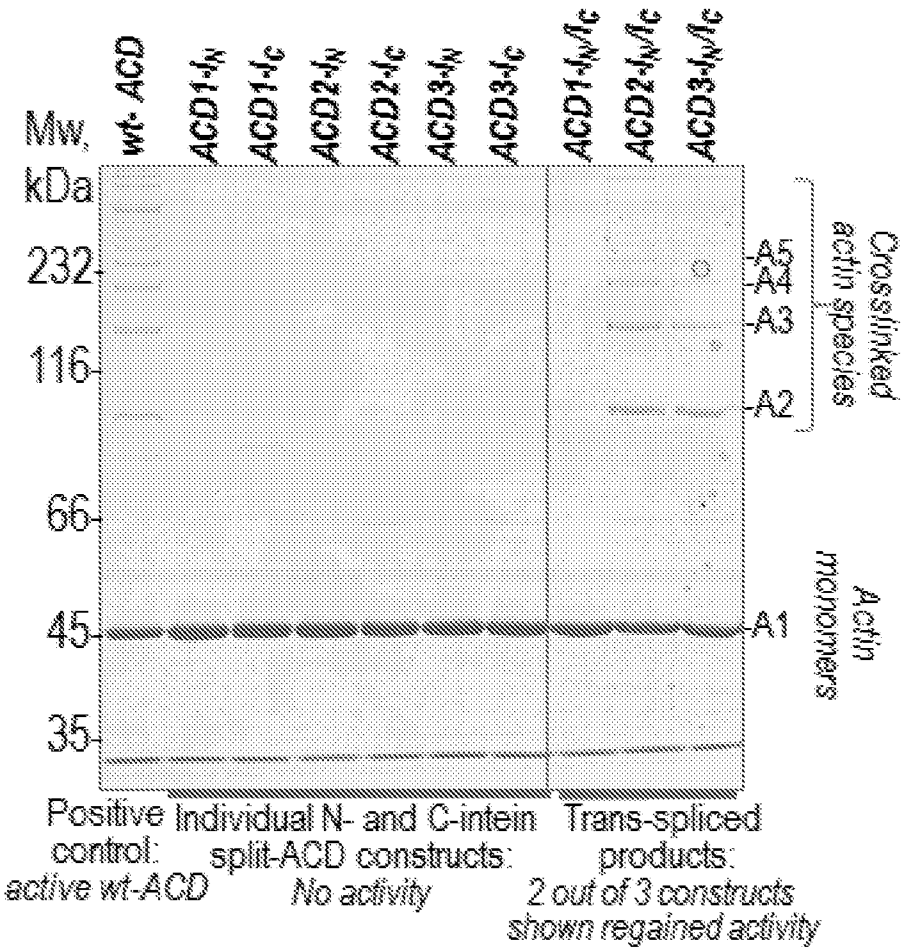

By following the above strategy, Actin Crosslinking Domain (ACD) of *Vibrio cholerae* was split at three different positions (FIG. 2C) and the N- and C-terminal parts of the toxin were fused to N- and C-intein sequences of $DnaE_{Npu}$ intein. All three split toxin variants showed loss of activity, which was regain for two of them upon trans-splicing in vitro. One of the two split pairs was tested in cell culture with U2OS cells stably expressing the N-terminal part of the GFP-toxin-intein construct (GFP-$ACD474_N$-$DnaE_N$). The cells were treated with the counterpart split-toxin $LF_N$-$ACD477_C$-$DnaE_C$ (200 nM) mixed with PA (100 nM). Following overnight incubation, cells expressing ~150-450 nM GFP-$ACD474_N$-$DnaE_N$, but not the control U2OS cells, got rounded consistent with the actin-crosslinking by a reconstituted ACD toxin. Similarly, 7 complimentary pairs of split Gelonin from *Gelonium multiflorum* ($LF_N$-$Gelonin_N$-$DnaE_N$ and LFn-$Gelonin_C$-$I_C$) have been constructed and expressed in *E. coli*. Most of toxin pairs resulted in soluble proteins, demonstrating a universal applicability of the splitting algorithm.

Example 2: Optimizing Intein Sequences to Better Serve the Goal of Cancer Cell Targeting

Experimental Design

Bacterial toxins are distinguished from the majority of other proteins by a set of distinct characteristics. First, most bacterial toxins share low thermodynamic stability (Kudryashova, E., et al. Biological chemistry 2017 398:1069-1085; Kudryashova, E. et al. Immunity 2014 41:709-721), allowing them to go through dramatic conformation changes required for the formation of a membrane pore or for crossing this pore (e.g., a pore formed by PA subunits of Atx). For a similar reason, most toxins have very low cysteine content, preventing stabilization by intra- and inter-molecular crosslinking. Since the split-intein sequences $DnaE_N$ and $DnaE_C$ are not originally designed for crossing membranes, they may interfere with this process hampering the usage of Atx delivery pathway. To test whether this is the case and to optimize the intein sequences for the goals of the proposal, all non-catalytic cysteine residues were removed by replacing them with Ala and Ser residues, depending on the context. Particularly, these experiments were aimed to reveal which part (N- or C-) of the split-toxin-intein pairs should be encoded in the virus and which can be efficiently translocated across the membrane using the Atx delivery.

Next, improved mutual recognition of the split-inteins was achieved by adding to their ends short (~20-a.a.) α-helices capable of forming high-affinity antiparallel coiled-coils (FIG. 2A). To facilitate the intein optimization, fusion proteins of the inteins with the ACD toxin of *Vibrio cholerae* are used—a toxin whose cell rounding activity is easier and faster to monitor and quantify than the activity of DTA.

Results

Fusion of the C-intein with $LF_N$-ACD (i.e., ACD toxin designed for intracellular delivery via the Atx entry pathway) did not negatively affect the ACD toxicity despite the presence of a single catalytic Cys in the C-intein sequence. In contrast, a fusion of the N-intein with $LF_N$-ACD inhibited toxicity at least ten fold, which could result from a more rigid structure of the N-intein part (Shah, N. H. et al. J Am Chem Soc. 2013 135:18673-18681), the presence of three cysteines, or both. Since one of the cysteines contributes to the catalysis, the mutation of the other two was optimized. There was a dramatic raise of toxicity, overall comparable to that of the toxin without inteins, without substantial loss in catalysis. Addition of the coiled coil helices to enforce high-affinity interaction between inteins (FIG. 2A) had negligible influence on their delivery. Similar results were obtained with fusion constructs of $LF_N$-DTA toxin, albeit detailed characterization of the delivery efficiencies is still in progress. These data suggest that the proposed approach offers substantial flexibility in delivering both parts of the split-toxin either as a protein, through a receptor-mediated entry pathway, or by a transduction of recombinant oncolytic virus.

Example 3: Reconstituting Functional Toxin in the Cytoplasm of Cancer Cells from its Benign Parts Separately Delivered Via DNA Transfection and as a Protein Via Cell Surface Receptors

Experimental Design

This example explores whether toxin can be reconstituted if one of its parts is delivered via transfection, while another as an inactive split-immunotoxin. Before moving to the virus-based delivery, transfection-based delivery is essential for proper characterization of the split-toxins, specifically to ensure that in the split state they do not have toxicity, which otherwise could be masked by the toxicity of the virus. Transiently transfected (TurboFect) cells were challenged by G418 antibiotic to select stably transfected clones. Protein synthesis inhibition due to the reconstitution of the full-length active toxin after the delivery of the second component was evaluated by the SUnSET assay (Schmidt, E. K. et al. Nature methods 2009 6:275-277), whereas overall toxicity was monitored using a modified MTS/PMS assay (Promega).

Cell lines: Of the four major classes of breast cancer cell lines, focus was on several $HER2^+$ (SK-BR-3, MDA-MB-361, BT-474) and triple negative breast cancers (TNBC: HCC1806, MDA-MB-231, MDA-MB-436, and MDA-MB-468). Targeting of the $HER2^+$ cells is straightforward due to the presence of the respective receptors on their surfaces, while targeting of TNBC cells is more challenging, but also potentially more impactful, given the poor prognosis of TNBC tumors.

Toxin delivery: Delivery of a complementary split-toxin part to the cytoplasm of cancer cells was achieved via receptors over-produced by cancer cells. For these experiments, focus was on delivery via (1) TEM8 (Tumor Endothelial Marker-8; over-expressed on tumor endothelial cells and many cancer cells (Gutwein, L. G., et al. Anticancer Res 2011 31:3417-3422), including TNBC MDA-MB-231, MDA-MB-436, and MDA-MB-468), (2) HER2 (over-expressed on all $HER2^+$ lines) (Smith, S. E., et al. Breast Cancer Res 2017 19:65; Krishnamurti, U. & Silverman, J. F. Adv Anat Pathol 2014 21:100-107), and (3) EGFR (abundant on the surface of various cancer cells (Smith, S. E., et al. Breast Cancer Res 2017 19:65; Nakai, K., et al. Am J Cancer Res 2016 6:1609-1623), including all the above TNBC lines). These cells were targeted via modified Atx entry pathways achieved by retargeting protective antigen (PA), the receptor-specific component of Atx, to cancer-specific receptors TEM8, HER2, and EGFR (Chen, K. H., et al. J Biol Chem. 2007 282:9834-9845; McCluskey, A. J., et al. Mol Oncol. 2013 7:440-451; Mechaly, A., et al. MBio. 2012 3(3)). As an alternative pathway, split-immunotoxin targeting mesothelin can be used (Alewine, C. et al. Mol Cancer Ther. 2014 13:2653-2661). Mesothelin is overexpressed in numerous solid tumors including 67% TNBC (Tchou, J. et al. Breast Cancer Res Treat. 2012 133:799-804) and its targeting by immunotoxins has shown promising results in clinical trials (Hassan, R. et al. Science translational medicine 2013 5:208ra147).

Results

SK-BR-3 cells are killed by picomolar (pM) concentrations of the full-length $LF_N$-DTA delivered via the HER2 receptor, but are not sensitive to the TEM8-dependent toxin in accordance with the receptor's presence at the cell surface. In contrast, osteosarcoma U2OS cells and TNBC MDA-MB-231 cells are sensitive to the TEM8-, but not to HER2-mediated toxin entry. Finally, TNBC MDA-MB-468 cells are resistant to HER2-based delivery and are affected only by relatively high (10 nM) concentrations of TEM8-entered toxin, suggesting that other entry portals (e.g., EGFR, mesothelin) have to be explored for these cells.

Figure 3:
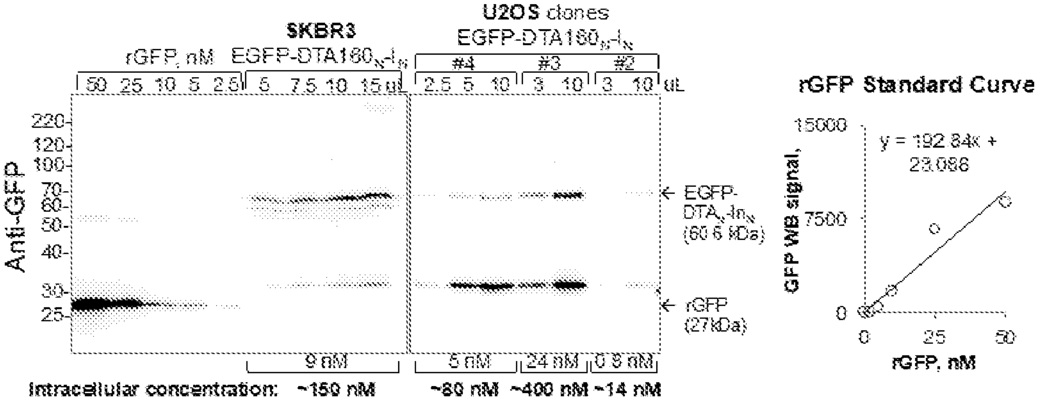
FIG. 3 depicts a quantitative anti-GFP Western blotting to assess EGFP-$DTA_N$-$DnaE_N$ intracellular concentration in stably transfected SK-BR-3 and U2OS clones. Recombinant GFP (rGFP) was titrated to create a standard curve for qauntitation.

Expression of the split-construct EGFP-$DTA_N$-$DnaE_N$ by stably transfected U2OS and SK-BR-3 cell lines was quantified using anti-GFP Western blotting with recombinant EGFP as a standard and the intracellular concentration of the full-length transfected construct was found to be in high nanomolar range in several cell clones (FIG. 3). Essentially, delivery of a complementary split-toxin part ($LF_N$-$DnaE_C$-$DTA_C$) to the cells expressing 150-400 nM (intracellular concentration) of EGFP-$DTA_N$-$DnaE_N$ caused potent cytotoxicity in U2OS and SK-BR-3 cells with $EC_{50}$ concentrations <10 pM (FIG. 4A, B). These $EC_{50}$ values are only slightly higher than those for full-length DTA and several times lower than those effective in clinical trials of mesothelin-targeting SS1P immunotoxin (Hassan, R. et al. Science translational medicine 2013 5:208ra147). Importantly, only the interaction of both parts of the toxin in the same cell confers toxicity, as neither the EGFP-$DTA_N$-$DnaE_N$ construct alone expressed in transfected cells nor the $LF_N$-$DnaE_C$-$DTA_C$ construct alone delivered to non-transfected cells have any negative influence on cell growth and proliferation in the absence of the counterparts (FIG. 4C, D). Also, specificity of the targeting is strictly controlled by a delivery pathway, as EGFP-$DTA_N$-$DnaE_N$-transfected SK-BR-3 cells (TEM8-negative/HER2-positive) are resistant to the TEM8-mediated, but not HER2-mediated delivery of the second component (FIG. 4C). Selectivity of the targeting may be further increased by selective production of the first split-toxin part by replicating oncolytic viruses in cancer cells.

Example 4: Reconstituting Functional Toxin from its Benign Parts Separately Delivered Via an Oncolytic Virus and Cell Surface Receptors

Experimental Design

With nearly a dozen of oncolytic viruses on different stages of clinical trials for breast and other solid tumors (Fukuhara, H. et al. Cancer Sci 2016 107:1373-1379), some may work better than others providing space for optimization. However, the concept feasibility is verified on HSV-Q virus, an HSV-1 derivative similar to the T-VEC (approved for treating melanomas (Rehman, H. et al. J Immunother Cancer 2016 4:53)). Expression under control of two distinct promoters is assessed: the immediate early 4/5 promoter (IE4/5; (Mahller, Y. Y., et al. Cancer Res. 2008 68:1170-1179)), ensures early and maximal production of the $DTA_N$-$DnaE_N$ split-toxin part and is expected to be most beneficial for the least permissive tumors; the late "gC" promoter, which is active only in cells with actively replicating viruses (Yamamoto, S. et al. Gene Ther 2006 13:1731-1736), is useful for moderately permissive tumors. The second half of the split-toxin ($LF_N$-$DnaE_C$-$DTA_C$; FIGS. 1 & 2) is delivered as discussed above. After initial experiments on pure cultures of breast cancer cells, mixed populations of breast cancer cells (listed above) and different types of normal cells of mammary origin (184B5, MCF 10A, MCF 12A, Hs578Bst, and primary HMEC) are tested. Normal cell lines are discriminated from the transformed ones by staining with CellTracker (Invitrogen) similar to as shown in FIG. 4C.

To achieve high levels of cancer-specific toxicity, virus MOI, toxin doses, delivery pathway, and the interval between addition of the virus and the immunotoxin are optimized. All three delivery pathways discussed above are explored. Levels of virus replication and $DTA_N$-$DnaE_N$ production at various MOI are evaluated by real time qPCR. Proper timing of split-toxin addition for trans-membrane delivery is critical for the efficient trans-splicing and therefore will be thoroughly assessed. Thus, a too early addition may result in intracellular degradation of the second component before the accumulation of sufficient qualities of the first, leading to a deficient trans-splicing and inefficient toxicity. The optimal delivery time can be delayed by 6-24 hours upon accumulation of sufficiently high level of the first half of the split-toxin in cancer cells. By this time, highly permissive cells may even be killed by the virus, but less permissive cells are conditioned to be poisoned by the split-DTA.

Example 5: Evaluating Targeting of Human Xenograft Breast Cancer Mouse Models by a Combined Action of an Oncolytic Virus and a Reconstituted Split-Toxin

Experimental Design

Ectopic and metastatic cell line-derived xenograft (CDX) models are created in nude mice (Envigo, IN) via established protocols (Browne, A. W., et al. PloS one 6:e19530) using HER2+ and TNBC lines with moderate to low permissiveness to HSV-Q and high sensitivity to the toxin. Each tumor is gender-matched with respect to donor-recipient. For each CDX model, study groups include control, virus or split-toxin only, and their combination therapy with the split-toxin component injected 24 and 48 hours post-infection. There is a 90% power to detect an additive effect of the combination when compared with each agent alone. Standard assessment of HSV-treatment efficacy includes (1) tumor size/volume measurements (n=10), (2) animal survival, with euthanasia required when tumors reach 10% body weight, (3) intratumoral virus replication (plaque assays or real-time PCR to quantify virus genomes), (4) microscopic morphology (n=2, at the same time points and upon euthanasia at the end of the experiment). For each tumor model, n=10 mice per group achieves 90% power to detect synergy, with a coefficient of variation (CV)=40% at a significant level of 0.05. The STR finger printing identity test and mycoplasma controls will be done once and twice per year, respectively. Animal experiments are performed blinded with respect to tumor measurements as they will be acquired by our animal technicians without knowledge of treatment groups.

Example 6

Experimental Design

Cancer cell lines most responsive to the proposed innovative strategy and least permissive to clearing by HSV-Q alone are identified. One of such lines is used to establish a localized (e.g., subcutaneous) cell line-derived xenograft (CDX) model in nude mice (Envigo, IN) via established protocols. The tumor is gender-matched with respect to donor-recipient. To ensure that the virus produces EGFP-$DTA_N$-$DnaE_N$ protein upon replication, animals with established tumors are treated with the HSV-Q/EGFP-$DTA_N$-$DnaE_N$ virus at an established dose. The production of the viral component of the split-is evaluated 3 and 5 days p.i. by i) visually observing the fluorescence of the dissected tumors and ii) analyzing the tumor and other tissues by western blotting probed with an anti-GFP antibody with a titration of purified GFP as a quantitative calibration control.

For the combined therapy studies, the virus injection is followed by injection of the PA/$LF_N$-$DnaE_C$-$DTA_C$ component (10:1 mole ratio) delivered intratumorally with the 24 and 48 hours post-infection delays. Study groups include control, intratumorally administered virus or split-toxin only, and their combination therapy with the split-toxin component. Standard assessment of HSV-treatment efficacy includes (1) tumor size/volume measurements (n=10) three times weekly, (2) animal survival, with euthanasia required when tumors reach 10% body weight, or animals reach IACUC guidelines, (3) intratumoral virus replication (plaque assays or real-time PCR to quantify virus genomes) at 1, 3, 7, 10 days to confirm virus delivery to and replication in tumors, (4) microscopic morphology (n=2, at the same time-points and upon euthanasia at the end of the experiment). Statistical confidence is controlled by a biostatistician, who will supervise the designs, power calculations and analyses for all of the experiments. The tumor volumes at the end of study are compared between virus and peptide combination and each of them alone and vehicle control. For each tumor model, n=10 mice per group achieves 90% power to detect a 2-fold difference (corresponding effect size 1.78), with a coefficient of variation (CV)=40% at a significant level of 0.017 (adjusting for 3 primary contrasts, t-test). These longitudinal data are analyzed by the mixed effect model followed by pairwise comparisons with Dunnet's method to adjust for multiplicity. Survival probabilities of groups are estimated by the Kaplan-Meier method and compared by the log-rank test. The STR fingerprinting identity and mycoplasma testing are performed once and twice per year, respectively. Animal experiments are performed blinded with respect to tumor measurements as they are acquired by animal technicians without knowledge of treatment groups. Data is reported using the ARRIVE guidelines.

Example 7: Exploring the Anthrax Toxin (Atx) Delivery Machinery Through Retargeting of Protective Antigen (PA) to Different Cell-Surface Receptors Verified the delivery of $LF_N$ACD and $LF_N$DTA toxins to cells through Atx delivery machinery using wild type PA (targeting both TEM8 and CMG2) and three retargeted PA variants specifically targeting TEM8, HER2, and EGFR, respectively.

Tested the delivery of $LF_N$ACD using newly created PA retargeted to mesothelin (MSLN) by fusion of mPA with the single chain fragment variable (scFv) of anti-MSLN antibody (~115 kDa): U2OS and MDA-MB-231, but not A549, (consistent with high level of MSLN expression in MDA-MB-231 and low level in A549) got rounded by $LF_N$ACD (2 nM)+mPA-MSLN (5 nM) following 24 h incubation period.

A panel of human cancer cell lines (Table 1) has been tested for expression of TEM8, HER2, and EGFR receptors for toxin delivery.

TABLE 1

| Cell line | Tumor origin | TEM8/CMG2 | TEM8 only | HER2 | EGFR |
|---|---|---|---|---|---|
| 143.98.2 | Osteosarcoma | + | + | − | + |
| A-549 | Lung carcinoma | + | + | + | − |
| CHLA-20 | Neuroblastoma | − | − | − | − |
| CHLA-90 | Neuroblastoma | − | − | − | + |
| F420 | Sarcoma (mouse) | + | + | − | − |
| H460 | Lung carcinoma | − | − | − | − |
| HCT-15 | Colorectal | − | − | + | + |
| Hs578T | Breast carcinoma | + | + | − | − |
| MCF7 | Breast carcinoma | − | − | − | − |
| MDA-MB-231 | Breast carcinoma | + | + | − | + |
| MDA-MB-436 | Breast carcinoma | − | − | + | + |
| MDA-MB-468 | Breast carcinoma | −/+ * | −/+ * | − | + |
| SJCRH30 | Rhabdomyosarcoma | + | + | − | − |
| SK-BR-3 | Breast cancer | − | − | + | −/+ * |
| U2OS | Osteosarcoma | + | + | − | − |

* Cell rounding is seen only 24 hours after treatment

Example 8: Exploring a Different Delivery Pathway Based on Diphtheria Toxin (DT) Instead of Atx Machinery Actin crosslinking domain (ACD) toxin was fused with truncated DT (devoid of majority of the catalytic domain (DTA) but with the preserved delivery components) to create ACD-DTR and tested for the delivery through DT pathway.

Preliminary cell studies show that 2.5 nM ACD-DTR induces cell rounding in all tested cell lines (U2OS, MDA-MB-231, and A549) following 24 h incubation period due to effective covalent crosslinking of actin molecules into oligomers.

Example 9: Exploring Splitting and Reconstitution of Toxins Other than DTA Toxin Actin crosslinking domain (ACD) toxin has been successfully split and reconstituted in vitro and in cell culture (FIG. 5).

Reconstruction of full length functional ACD toxins from two split pieces in live cells has also been successfully achieved. Specifically, osteosarcoma U2OS cells stably transfected with EGFP-ACD474$_N$-I$_N$ were treated with its counterpart LF$_N$-ACD477$_C$-I$_C$ (200 nM) mixed with PA (100 nM). Following overnight incubation, cells expressing ~150-450 nM GFP-ACD474$_N$-I$_N$, but not the control U2OS cells, got rounded consistent with the ACD toxicity.

Splitting and reconstitution of Gelonin: 7 complimentary pairs of LF$_N$-Gelonin$_N$-I$_N$ and LF$_N$-Gelonin$_C$-I$_C$ have been constructed and expressed in *E. coli*. At least three split positions generated soluble constructs.

Example 9: Exploring an Oncolytic Virus Delivery of a Split Toxin DNA Using HSV-1 Variant HSV-Q oncolytic virus containing a split-DTA toxin part (EGFP-DTA$_N$-DnaE$_N$) split-DTA toxin part has been generated. A panel of human cancer cell lines were infected at different MOI with the HSV-Q virus encoding the EGFP-DTA$_N$-DnaE$_N$ toxin. Expression of the EGFP-fused split-toxin component in all tested cancer cell lines was confirmed by anti-GFP and anti-DTX Western blotting (FIG. 5) and evident from the characteristic green fluorescence (FIGS. 6A and 6C) and subsequent cell rounding, albeit the fraction of affected cells and time to rounding varied depending on MOI and the cell type. Addition of the corresponding LF$_N$-DnaE$_C$-DTA$_C$ toxin (10 nM) along with a modified PA (25 nM) three to five hours after the infection caused notable decrease in the production of EGFP-DTA$_N$-DnaE$_N$ (quantified in FIG. 7) owing to inhibition of protein synthesis 1 day post-treatment. Cell toxicity was measured by the ATP level (FIG. 6B; U2OS cells) or by monitoring a reducing potential (FIG. 6D; SK-BR-3 cells). To avoid interference with the virus propagation, use of toxins acting via mechanisms independent of protein synthesis inhibition will be explored.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A system, comprising a first fusion protein and a recombinant vector comprising a nucleic acid sequence encoding a second fusion protein,
wherein the first fusion protein comprises
a first split intein,
a first extein that comprises a first non-functional fragment of a polypeptide toxin, and
a ligand for receptor-mediated cell entry;
wherein the second fusion protein comprises
a second split intein, and
a second extein that comprises a second non-functional fragment of the toxin; and
wherein receptor-mediated internalization of the first fusion protein and recombinant expression of the nucleic acid encoding the second fusion protein in the cytoplasm of a cell results in trans-splicing of the first extein and the second extein to form a functional toxin in the cell.

2. The system of claim 1,
wherein the first split intein is a C-intein, the second split intein is an N-intein, the first extein comprises a C-terminal fragment of the toxin, and the second extein comprises an N-terminal fragment of the toxin; or
wherein the first split intein is an N-intein, the second split intein is a C-intein, the first extein comprises an N-terminal fragment of the toxin, and the second extein comprises a C-terminal fragment of the toxin.

3. The system of claim 1, wherein the toxin is an exotoxin.

4. The system of claim 3, wherein the exotoxin is a diphtheria toxin.

5. The system of claim 1, wherein the ligand comprises a receptor binding moiety of the toxin.

6. The system of claim 1, wherein the ligand comprises a binding moiety heterologous to the toxin.

7. The system of claim 6, wherein the ligand comprises the N-terminal fragment of anthrax Lethal Factor (LFN).

8. The system of claim 7, wherein the toxin is selected from the group consisting of pseudomonas toxin, shiga toxin, cholera toxin, and diphtheria toxin.

9. The system of claim 1, wherein the first fusion protein comprises the formula NH3-ExtN-IntN-Lig-COOH, NH3-Lig-ExtN-IntN-COOH, NH3-IntC-ExtC-Lig-COOH, or NH3-Lig-IntC-ExtC-COOH, wherein "ExtN" comprises the N-terminal fragment of a toxin,
wherein "ExtC" comprises the C-terminal fragment of a toxin,
wherein "IntN" comprises a N-intein,
wherein "IntC" comprises a C-intein,
wherein "Lig" comprises a ligand configured for receptor-mediated cell entry, and
wherein "-" comprises a linker or peptide bond.

10. The system of claim 1, wherein the ligand comprises the N-terminal fragment of anthrax Lethal Factor (LFN), further comprising a pore-forming protective antigen (PA) subunit modified to target a specific receptor.

11. The system of claim 1, wherein the receptor is a cancer-specific receptor.

12. The system of claim 11, wherein the receptor is selected from the group comprising TEM8, EGFR, HER2, mesothelin, and TAG-72.

13. The system of claim 1, wherein the recombinant vector is based on an oncolytic virus selected from adenovirus, vesicular stomatitis virus (VSV), Newcastle disease virus (NDV), Herpes simplex virus (HSV), and vaccinia virus.

14. A method for treating cancer in a subject, comprising administering to the subject a first composition comprising a fusion protein and a second composition comprising an oncolytic virus comprising a recombinant vector having nucleic acid encoding a second fusion protein, wherein the first fusion protein comprises a first split intein, a first extein that comprises a first non-functional fragment of a toxin, and a ligand for receptor-mediated cell entry;

wherein the second fusion protein comprises a second split intein, and a second extein that comprises a second non-functional fragment of the toxin; and wherein co-localization of the first fusion protein and the second fusion protein in a cell results in trans-splicing of the first extein and the second extein to form a functional toxin in the cancer cell, thereby treating the cancer.

15. The method of claim 14, wherein the first split intein is a C-intein, the second split intein is an N-intein, the first extein comprises a C-terminal fragment of the toxin, and the second extein comprises an N-terminal fragment of the toxin, or wherein the first split intein is an N-intein, the second split intein is a C-intein, the first extein comprises an N-terminal fragment of the toxin, and the second extein comprises a C-terminal fragment of the toxin.

* * * * *